United States Patent
Khettal et al.

(10) Patent No.: US 10,816,790 B2
(45) Date of Patent: Oct. 27, 2020

(54) RELAY OPTICAL SYSTEM FOR A RIGID ENDOSCOPE

(71) Applicant: avateramedical GmbH, Jena (DE)

(72) Inventors: Ali Khettal, Berlin (DE); Fabian Weise, Berlin (DE)

(73) Assignee: avateramedical GmbH, Berlin (DE)

( * ) Notice: Subject to any disclaimer, the term of this patent is extended or adjusted under 35 U.S.C. 154(b) by 86 days.

(21) Appl. No.: 16/008,782

(22) Filed: Jun. 14, 2018

(65) Prior Publication Data

US 2018/0364473 A1 Dec. 20, 2018

(30) Foreign Application Priority Data

Jun. 16, 2017 (DE) .................. 10 2017 113 271

(51) Int. Cl.
| | |
|---|---|
| *G02B 23/24* | (2006.01) |
| *A61B 1/00* | (2006.01) |
| *A61B 1/002* | (2006.01) |
| *A61B 1/055* | (2006.01) |
| *G02B 13/00* | (2006.01) |
| *H04N 5/225* | (2006.01) |
| *G02B 1/11* | (2015.01) |
| *G02B 5/00* | (2006.01) |

(52) U.S. Cl.
CPC .......... *G02B 23/2446* (2013.01); *A61B 1/002* (2013.01); *A61B 1/00193* (2013.01); *A61B 1/055* (2013.01); *G02B 13/0095* (2013.01); *G02B 23/243* (2013.01); *G02B 23/2415* (2013.01); *G02B 1/11* (2013.01); *G02B 5/005* (2013.01); *H04N 2005/2255* (2013.01)

(58) Field of Classification Search
CPC ............ G02B 13/0095; G02B 23/2446; G02B 23/2415; G02B 23/243; G02B 1/11; G02B 5/005; H04N 2005/2255; A61B 1/00193; A61B 1/002; A61B 1/055
USPC .......................................... 359/435
See application file for complete search history.

(56) References Cited

U.S. PATENT DOCUMENTS

| | | | |
|---|---|---|---|
| 5,557,454 A | 9/1996 | Takahaski | |
| 5,684,629 A * | 11/1997 | Leiner ................... | A61B 1/002 359/362 |
| 5,805,345 A | 9/1998 | Nagoka | |
| 6,490,085 B1 | 12/2002 | Zobel | |
| 2001/0039371 A1 * | 11/2001 | Forster ............... | G02B 23/2446 600/176 |
| 2005/0119529 A1 * | 6/2005 | Farr ....................... | A61B 1/055 600/160 |

(Continued)

FOREIGN PATENT DOCUMENTS

| | | |
|---|---|---|
| DE | 102013209956 A1 | 4/2014 |
| DE | 102016106518 A1 | 10/2017 |

(Continued)

*Primary Examiner* — Collin X Beatty
(74) *Attorney, Agent, or Firm* — McGarry Bair PC

(57) ABSTRACT

A relay optical system for a rigid endoscope has two identically formed lens systems which are arranged symmetrically to each other with respect to a plane of symmetry that is perpendicular to the optical axis. The lens systems each comprise a first biconvex lens, a biconcave lens, a rod lens having a convex lens surface facing the plane of symmetry and a concave lens surface facing away from the plane of symmetry, and a second biconvex lens, in this order as viewed from the plane of symmetry.

15 Claims, 2 Drawing Sheets

(56) References Cited

U.S. PATENT DOCUMENTS

| | | | | |
|---|---|---|---|---|
| 2014/0343362 A1* | 11/2014 | Tesar | ............... | A61B 1/002 600/181 |
| 2015/0168710 A1* | 6/2015 | Zobel | ............ | A61B 1/00105 348/45 |
| 2015/0256721 A1* | 9/2015 | Moore | ............ | G02B 23/2446 348/65 |
| 2017/0293139 A1* | 10/2017 | Rehe | ............ | G02B 23/2453 |

FOREIGN PATENT DOCUMENTS

| | | |
|---|---|---|
| EP | 3229056 A1 | 10/2017 |
| WO | 2015131278 A1 | 9/2015 |

* cited by examiner

RELAY OPTICAL SYSTEM FOR A RIGID ENDOSCOPE

CROSS REFERENCE TO RELATED APPLICATION

This application claims the benefit of German Application DE 10 2017 113 271.0, filed on Jun. 16, 2017, which is incorporated herein in its entirety.

BACKGROUND

The invention relates to a relay optical system for a rigid endoscope, comprising two identically formed lens systems which are arranged symmetrically to each other with respect to a plane of symmetry that is perpendicular to the optical axis. Further, the invention relates to an endoscope comprising a relay system having at least one such relay optical system.

Endoscopes are in particular used in minimally invasive surgery to allow the operating surgeon insight into the body region in which the operating field is situated. Both monocular endoscopes and stereoscopic endoscopes are used, the latter providing a three-dimensional impression of the depth via two optical channels, which is not possible with monocular endoscopes.

At the distal end of an endoscope shaft, typically an objective lens is arranged, which collects the light originating from the object to be observed and generates a real intermediate image of the object. This intermediate image is transmitted by means of an optical relay system arranged downstream of the objective lens to the proximal end of the endoscope shaft. At the proximal end of the endoscope shaft, an eyepiece is arranged which images the real intermediate image either for the human eye or by means of a camera objective lens onto a sensor surface.

An optical relay system for use in an endoscope should have a high optical quality with a small diameter. While in flexible endoscopes often light guides, e.g. bundles of glass fibers, are used for this purpose, relay systems with rod lenses have prevailed for use in rigid endoscopes. In particular, rod lenses produced from special optical glasses have a higher optical quality than flexible light guides.

In document U.S. Pat. No. 5,557,454 A, a rigid endoscope is disclosed, which implements by means of rod lenses the optical image transport from an objective lens mounted distally in the endoscope shaft to a proximally arranged eyepiece.

From document U.S. Pat. No. 6,490,085 B1, an optical relay system for a rigid endoscope is known, comprising two lens systems which are arranged symmetrically with respect to the plane of symmetry that is perpendicular to the optical axis.

In document DE 10 2013 209 956 A1, a rigid stereoscopic endoscope is disclosed, in which the image transport from a proximally mounted objective lens to a distally mounted sensor surface is again implemented using rod lenses.

In document WO 2015/131278 A1, a system provided for the image transport for broad-band imaging is described, which is composed of mirror-symmetrically arranged rod lenses and spherical lenses.

The optical relay systems known from the prior art correct imaging errors either not at all or in any case not sufficiently. In particular, the known optical relay systems have a high image field curvature which can be corrected only with difficulties with downstream optical systems. Known optical relay systems are additionally only designed for a certain endoscope overall length.

SUMMARY OF THE INVENTION

The object of the invention is to specify a relay optical system for a rigid endoscope, which has a simple and compact design and at the same time corrects image errors, in particular the image field curvature, to the greatest possible extent.

This object is solved by a relay optical system having the features of claim 1 and an endoscope having the features of claim 7. Advantageous developments are specified in the dependent claims.

The inventive relay optical system comprises two identically formed lens systems which are arranged symmetrically to each other with respect to a plane of symmetry that is perpendicular to the optical axis. The lens systems each include a first biconvex lens, a biconcave lens, a rod lens having a convex lens surface facing the plane of symmetry and a concave lens surface facing away from the plane of symmetry, and a second biconvex lens, in this order as viewed from the plane of symmetry. As a result, a simple and compact structure of the relay optical system is achieved.

By the symmetric (mirror-image) arrangement of the identically formed lens systems, it is possible to correct the chromatic aberration that occurs in a lens system by the other lens system to the greatest possible extent. The correction of the chromatic aberration in particular makes it possible to successively arrange several relay optical systems within one relay system without the chromatic overall aberration of the relay system becoming too large.

The inventive relay optical system further has the advantage of a comparably low production and assembly cost in that only a few different component parts are used.

The specific design of the relay optical system also makes it possible that an image field curvature, caused for example by an objective lens arranged upstream of the relay optical system, is corrected by the relay optical system itself. In particular in a relay system including an arbitrary number of successively arranged relay optical systems, thus the image field curvature can be corrected almost completely. Further, by the correction of the image field curvature in the inventive relay optical system, an eyepiece arranged at the image-side of the relay optical system can be designed more compact than in endoscopes known up to now since in the present case the image field curvature is corrected in the relay optical system itself and not, as usual, in the eyepiece.

In an advantageous development, the first biconvex lens, the biconcave lens, the rod lens and/or the second biconvex lens of the respective lens system are cemented to each other. It is particularly advantageous to cement all aforementioned lenses to one single component part. In the following, this component part is also referred to as cemented rod lens system. By using cemented rod lens systems, the production and assembly cost can be reduced significantly.

In a further advantageous development, the rod lens of the respective lens system is composed of crown glass. Due to its good optical transmission properties, in particular the use of barium crown glass is advantageous for a relay optical system.

Preferably, the first biconvex lens, the biconcave lens and/or the second biconvex lens of the respective lens system are made of flint glass. The high dispersion of flint glasses allows the construction of cemented rod lens systems with desired achromatic properties, in particular by the combination of lighter and heavier flint glasses that have different Abbe numbers and refractive indices.

Advantageously, the first biconvex lens and/or the second biconvex lens of the respective lens system have an antireflection coating, in particular on their non-cemented surface. This in particular serves to increase the optical transmission and to minimize scattered light and thus to improve the optical quality of the relay optical system. An increase of the optical transmission makes it possible to connect several relay optical systems in series without significant light loss.

In a further advantageous embodiment, a stop is arranged in the plane of symmetry to limit the aperture of the relay optical system.

A further aspect of the invention relates to an endoscope comprising a relay system with at least one relay optical system of the type described above.

In an advantageous embodiment, the endoscope comprises a rigid endoscope shaft in which the relay optical system is arranged.

In a particularly advantageous embodiment, the relay system comprises at least one relay module including several relay optical systems of the above-described type arranged successively along the optical axis.

In a further advantageous embodiment, the relay system comprises two relay modules forming a stereoscopic arrangement. Thus, stereoscopic observations are possible by way of the endoscope.

The inventive optical design in particular comprises a combination of lens elements and a rod lens within a cemented group (rod lens system) and a combination of two rod lens systems into one relay optical system. The radii and materials of the individual lenses are preferably matched to each other such that the so-called Seidel aberrations are corrected particularly well. In doing so, in particular the Petzval sum as a measure for the image field curvature is minimized. By using two identical rod lens systems in reversed order, moreover the chromatic aberration of the first rod lens system can be compensated by the second rod lens system. Further, not only the intermediate images, which optically limit a relay optical system, can be corrected particularly well, but also the pupil imaging which is transferred from one relay optical system into the next relay optical system can be corrected.

Further features and advantages result from the following description which explains the invention in more detail on the basis of embodiments in connection with the enclosed Figures.

DRAWINGS

DESCRIPTION

Figure 1:
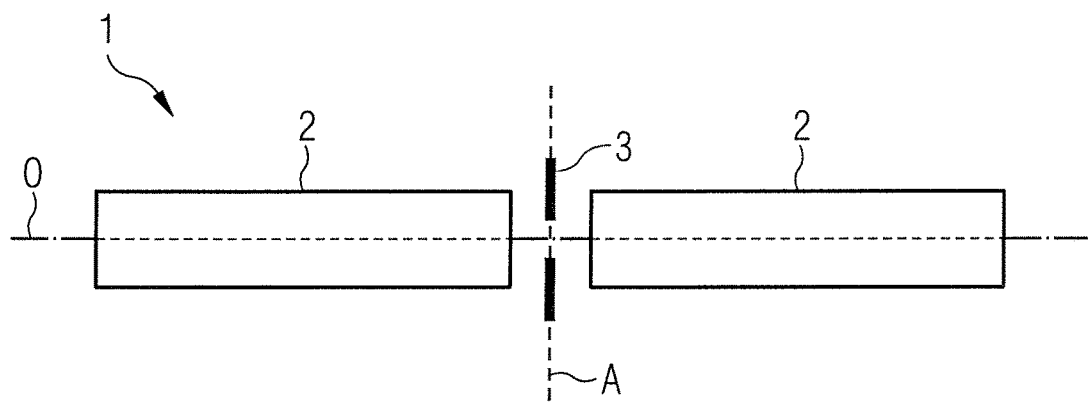
FIG. 1 shows a relay optical system for a rigid endoscope according to one embodiment.

FIG. 1 shows an embodiment of a relay optical system 1 for use in a rigid endoscope. The relay optical system 1 comprises two identically formed lens systems 2 and a stop 3 which is arranged between the lens systems 2 in a plane A that is perpendicular to the optical axis O of the endoscope. Both lens systems 2 of the relay optical system 1 are formed mirror-symmetrically to each other with respect to the plane A.

Figure 2:
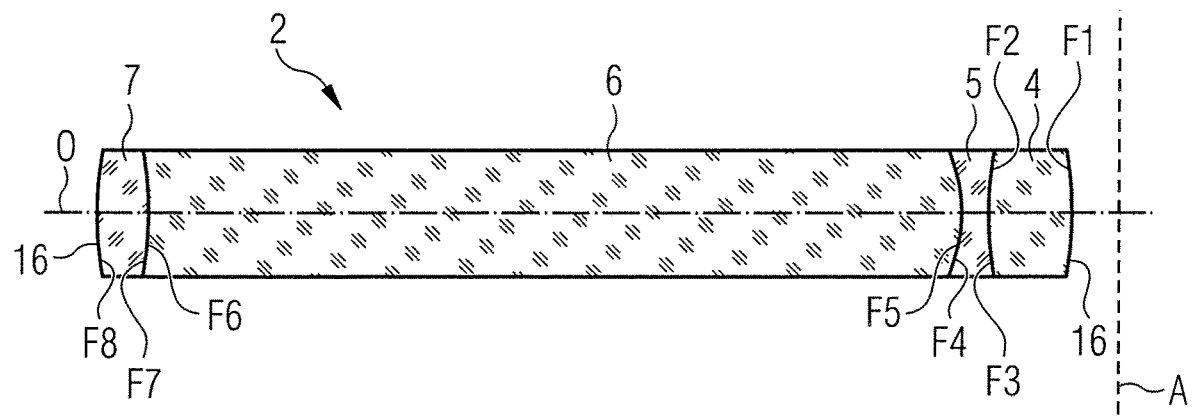
FIG. 2 shows an embodiment of a lens system which is part of the relay optical system according to FIG. 1.

In FIG. 2, one of the two identically formed lens systems 2 according to FIG. 1 is schematically illustrated. As viewed from the plane A, the lens system 2 comprises a first biconvex lens 4, a biconcave lens 5, a rod lens 6 and a second biconvex lens 7. The first biconvex lens 4 has two convex surfaces F1, F2. The biconcave lens 5 has two concave surfaces F3, F4. The rod lens 6 has a convex surface F5 facing the plane A and a convex surface F6 facing away from the plane A. The second biconvex lens 7 has two convex surfaces F7, F8.

The surface F2 of the first biconvex lens 4 that faces away from the plane A is cemented to the surface F3 of the biconcave lens 5 that faces the plane A to form one single optically effective surface. The surface F4 of the biconcave lens 5 that faces away from the plane A is cemented to the surface F5 of the rod lens 6 that faces the plane A. The surface F6 of the rod lens 6 that faces away from the plane A is cemented to the surface F7 of the second biconvex lens 7 that faces the plane A. Thus, the lens system 2 forms one single component part.

The non-cemented lens surfaces F1, F8 of the first biconvex lens 4 and the second biconvex lens 7, respectively, further each have an antireflection coating 16. These serve to reduce scattered light.

Table 1 shows the lens data of the relay optical system 1 according to FIG. 1 with the two identical lens systems 2 according to FIG. 2 arranged symmetrically about the stop 3. The optically effective surfaces of the relay optical system 1 are numbered in Table 1 with 1 to 10 from the object side. The associated reference signs according to FIG. 2 are indicated in parentheses. All dimensions and all information regarding the length are expressed in the unit [mm]. The names of the glasses are in accordance with the nomenclature of Schott.

TABLE 1

| Surface | Radius | Thickness | Glass | Diameter |
| --- | --- | --- | --- | --- |
| Object | Indefinite | 0 | | 2.5 |
| Aperture stop | Indefinite | 4.40117 | | 2.5 |
| 1 (F8) | 25.18 | 1.3 | N-LASF41 | 3.6 |
| 2 (F6, F7) | −14.3 | 23.7 | N-BAK1 | 3.6 |
| 3 (F4, F5) | −4.475 | 0.8 | N-KZFS11 | 3.6 |
| 4 (F2, F3) | 13.455 | 2.3 | N-LASF44 | 3.6 |
| 5 (F1) | −18.265 | 1.979656 | | 3.6 |
| Stop (3) | Indefinite | 1.979656 | | 3.6 |
| 6 (F1) | 18.265 | 2.3 | N-LASF44 | 3.6 |
| 7 (F2, F3) | −13.455 | 0.8 | N-KZFS11 | 3.6 |
| 8 (F4, F5) | 4.475 | 23.7 | N-BAK1 | 3.6 |
| 9 (F6, F7) | 14.3 | 1.3 | N-LASF41 | 3.6 |
| 10 (F8) | −25.18 | 4.40117 | | 3.6 |
| Image | −12.5 | | | 2.513237 |

Figure 3:
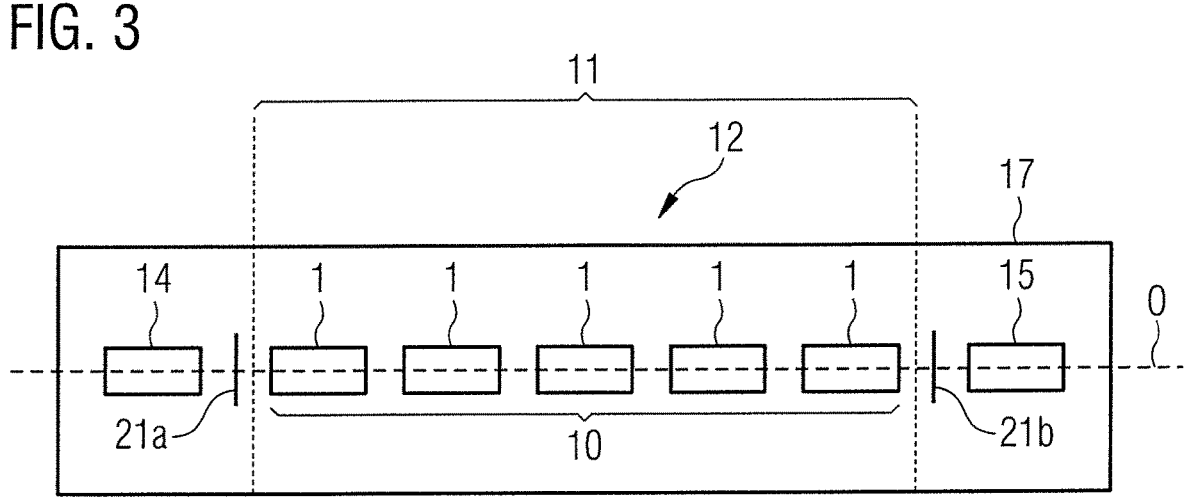
FIG. 3 shows an embodiment of a monocular endoscope including several relay optical systems according to FIG. 1.

One possible embodiment of a monocular endoscope 12 is schematically illustrated in FIG. 3. It comprises a distally arranged objective lens 14, an optical relay system 11 with a relay module 10 and a proximally arranged eyepiece 15. The endoscope 12 further comprises a shaft 17 in which the afore-mentioned component parts or optical elements 10, 14 and 15 are arranged. The relay module 10 includes several relay optical systems 1 according to FIG. 1 which are successively arranged along the optical axis O.

The functioning of the endoscope 12 shown in FIG. 3 is in particular such that the objective lens 14 arranged at the distal end of the endoscope 12 generates a first intermediate image 21a of the object to be observed. The relay module 10 images the distal first intermediate image 21a onto a proximal second intermediate image 21b. In doing so, the relay system 11 or the relay module 10 quasi transfers the first intermediate image 21a from the distal to the proximal end of the endoscope 12. The eyepiece 15 arranged at the proximal end of the endoscope 12 finally images the second intermediate image 21b onto a camera sensor not shown in FIG. 3.

The relay optical systems 1 of the relay module 10, each comprising two identical lens systems 2 according to FIG. 2, are in particular self-correcting with respect to the chromatic aberration. That means that each of the relay optical systems 1 is, when seen individually, almost completely corrected with respect to the chromatic aberration. This makes it possible to successively arrange a plurality of relay optical systems 1 within the relay module 10, without the chromatic overall aberration of the relay system 11 becoming too large. As a result, the endoscope 12 can be implemented in different overalls lengths with substantially the same optical quality.

Further, the correction of the image errors does not have to be accomplished by the eyepiece 15 arranged downstream of the relay module 10 either. Thus, the eyepiece 15 can have a particularly compact structure.

The individual relay optical systems 1 of the relay system 11 or the relay module 10 each form an optical inverting system having an image scale of −1. Since the relay optical systems 1 are arranged in the relay module 10 in an odd number (e.g. five), the relay system 11 forms an optical system with an image scale of +1.

Figure 4:
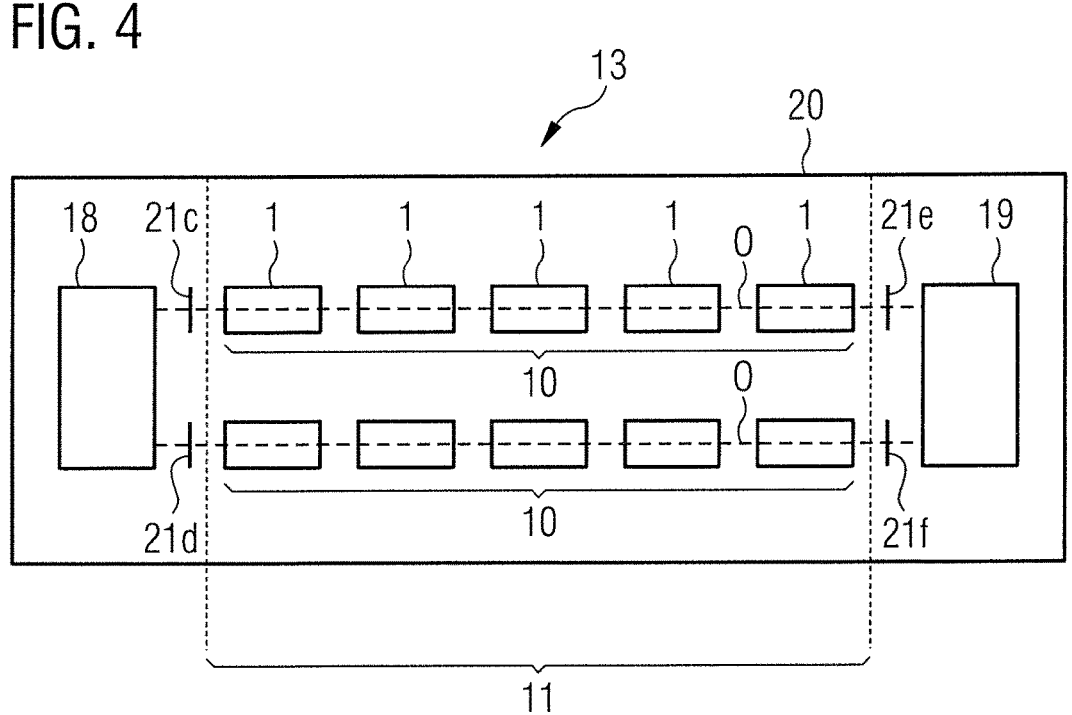
FIG. 4 shows an embodiment of a stereoscopic endoscope including several relay optical systems according to FIG. 1.

An embodiment of a stereoscopic endoscope 13 is schematically illustrated in FIG. 4. In contrast to the monocular endoscope 12 illustrated in FIG. 3, the stereoscopic endoscope 13 has two optical channels. The stereoscopic endoscope 13 has a shaft 20 in which, as viewed from the distal end, an objective lens 18, a stereoscopic relay system 11 with two relay modules 10 and a proximally arranged eyepiece 19 are arranged.

In the stereoscopic relay system 11, each time one of the two relay modules 10 is assigned to one of the two optical channels. Each of the two relay modules 10 images a distal intermediate image 21c and 21d, respectively, which is generated by the objective lens 18, onto a second proximal intermediate image 21e and 21f, respectively. The proximal intermediate images 21e and 12f, respectively, generated in this way, are then imaged by the eyepiece 19 onto a camera sensor not illustrated in FIG. 4.

The afore-mentioned embodiments according to FIGS. 3 and 4 are only examples. Thus, in particular the number of the relay optical systems 1 is neither restricted to an odd number nor specifically to the number five.

The stereoscopic endoscope 13 according to FIG. 4 provides a shared objective lens 18 for the two optical channels. In an alternative embodiment, a separate objective lens may be assigned to each individual channel.

The invention claimed is:

1. A plurality of identical relay optical systems for a rigid endoscope, arranged successively along an optical axis, each relay optical system comprising two identically formed lens systems which are arranged symmetrically to each other with respect to a plane of symmetry that is perpendicular to the optical axis, characterized in that the lens systems each comprise a first biconvex lens, a biconcave lens, a rod lens having a convex lens surface facing the plane of symmetry and a concave lens surface facing away from the plane of symmetry and a second biconvex lens, in this order as viewed from the plane of symmetry.

2. The relay optical system according to claim 1, characterized in that at least two of the first biconvex lens, the biconcave lens, the rod lens or the second biconvex lens of the respective lens system are cemented to each other.

3. The relay optical system according to claim 1, characterized in that the rod lens of the respective lens system is made of crown glass.

4. The relay optical system according to claim 1, characterized in that at least one of the first biconvex lens, the biconcave lens, or the second biconvex lens of the respective lens system is made of flint glass.

5. The relay optical system according to claim 1, characterized in that at least one of the first biconvex lens or the second biconvex lens of the respective lens system has an antireflection coating.

6. The relay optical system according to claim 1, characterized by a stop which is arranged in the plane of symmetry.

7. An endoscope comprising a relay system with at least two identical relay systems arranged successively along an optical axis, each relay optical system having two identically formed lens systems which are arranged symmetrically to each other with respect to a plane of symmetry that is perpendicular to the optical axis, characterized in that the lens systems each comprise a first biconvex lens, a biconcave lens, a rod lens having a convex lens surface facing the plane of symmetry and a concave lens surface facing away from the plane of symmetry and a second biconvex lens, in this order as viewed from the plane of symmetry.

8. The endoscope according to claim 7, comprising a rigid endoscope shaft in which the relay system is arranged.

9. The endoscope according to claim 7, characterized in that the relay system comprises at least one relay module having more than one relay optical system arranged successively along the optical axis.

10. The endoscope according to claim 9, characterized in that the relay optical system comprises two relay modules forming a stereoscopic arrangement.

11. The endoscope according to claim 7, characterized in that at least two of the first biconvex lens, the biconcave lens, the rod lens or the second biconvex lens of the respective lens system are cemented to each other.

12. The endoscope according to claim 7, characterized in that the rod lens of the respective lens system is made of crown glass.

13. The endoscope according to claim 7, characterized in that at least one of the first biconvex lens, the biconcave lens, or the second biconvex lens of the respective lens system is made of flint glass.

14. The endoscope according to claim 7, characterized in that at least one of the first biconvex lens or the second biconvex lens of the respective lens system has an antireflection coating.

15. The endoscope according to claim 7, characterized by a stop which is arranged in the plane of symmetry.

* * * * *